(12) United States Patent
DuBois

(10) Patent No.: US 8,197,801 B2
(45) Date of Patent: Jun. 12, 2012

(54) USE OF COMPOUNDS FOR THE PRESERVATION OF THE HUMAN OR ANIMAL BODY AND COMPOSITIONS COMPRISING SAME

(75) Inventor: Jean-Luc DuBois, Millery (FR)

(73) Assignee: Arkema France, Colombes (FR)

( * ) Notice: Subject to any disclaimer, the term of this patent is extended or adjusted under 35 U.S.C. 154(b) by 1195 days.

(21) Appl. No.: 11/963,244

(22) Filed: Dec. 21, 2007

(65) Prior Publication Data

US 2008/0166315 A1    Jul. 10, 2008

(30) Foreign Application Priority Data

Dec. 27, 2006 (FR) ..................... 06 11459

(51) Int. Cl.
*A01N 1/00* (2006.01)
*C07C 43/32* (2006.01)

(52) U.S. Cl. ......................... 424/75; 568/613

(58) Field of Classification Search ........................ None
See application file for complete search history.

(56) References Cited

U.S. PATENT DOCUMENTS

| 4,053,590 | A | * | 10/1977 | Bonsen et al. | ............... 514/13.4 |
| 5,350,670 | A | * | 9/1994 | Yeh | ............................. 435/1.1 |
| 6,387,360 | B1 | * | 5/2002 | Garrett | .......................... 424/75 |

OTHER PUBLICATIONS

Bedino (CHAMPION® Expanding Encyclopedia of Mortuary Practices, No. 649, 2614-2632, 2003).*
Search Report for French Patent Application No. 0611459 dated May 23, 2007.
Database WPI Week 200004, Derwent Publications Ltd., London GB; AN 2000-051485, XP002434828 & RU 2116725 C1 (Gaivoronskii et al.) Aug. 10, 1998.

* cited by examiner

*Primary Examiner* — David J Blanchard
*Assistant Examiner* — Tigabu Kassa
(74) *Attorney, Agent, or Firm* — McDonnell Boehnen Hulbert & Berghoff LLP

(57) ABSTRACT

The present invention relates to the use of at least one compound of formula (I) R—($OCH_2$)n—OR' in which R and R', identical or different, represent a linear or branched alkyl radical comprising 1 to 5 carbon atoms and n is an index with a value comprised between 1 and 8, and/or at least one dialdehyde acetal type compound for the preservation of the human or animal body and/or the embalming of dead bodies. It also relates to a composition comprising same and a process for preserving a human or animal body and/or embalming a dead body comprising the administration of the composition to the dead body in particular by injection, perfusion, immersion or topical application.

9 Claims, No Drawings

USE OF COMPOUNDS FOR THE PRESERVATION OF THE HUMAN OR ANIMAL BODY AND COMPOSITIONS COMPRISING SAME

This application claims priority from French patent application FR 0611459, filed on Dec. 27, 2006.

The present invention relates to the field of the preservation of human or animal cadavers. More particularly, the invention relates to a novel use, for non-therapeutic purposes, of at least one compound of the POM (PolyOxyMethylene dialkyl ether) type and/or of dialdehyde acetals for preserving and/or embalming a human or animal body.

The embalming of a dead body is a practice requested by the families of the deceased in order to preserve an acceptable appearance for the body until its burial or cremation. However, under certain circumstances, this operation can become obligatory, in particular in the case of international movements of the body, transport of the body before cremation in coffins with walls thinner than those intended to be buried, or even in the absence of a coffin, in certain cases of returning home the bodies of individuals who have died in hospital, and also in certain cases placing them in a temporary vault.

Moreover, the hygienic preservation of bodies the modern and effective means of avoiding the propagation of diseases by the living coming into contact with the dead, as well as pollution and soiling of objects and surroundings.

Different compounds are known which are used for embalming and/or preserving human or animal cadavers. In particular, phenol and aldehydes such as formaldehyde and glutaraldehyde (1,5-pentanedial) are commonly used in this field. However, these compounds are foul-smelling, highly toxic and have a tendency to leave the treated body in a rigid state.

The French patent FR 1 457 037 discloses a composition for preserving dead animal bodies comprising δ-lactones which contain an additional oxygen heteroatom in the nucleus. This composition can be applied to the cadaver by immersion, infusion or injection.

The American patent U.S. Pat. No. 5,827,511 describes a composition which can be injected by arterial route, comprising glutaraldehyde, at least one aromatic ether of ethanol, at least one hydrating agent such as ethylene glycol and at least one alcohol.

The patent EP 1 127 490 describes a composition comprising at least glycerol and, as active ingredient, an aqueous-alcoholic propolis extract. This composition can be painted onto the cadaver or injected by arterial route.

The patent WO2004/093541 discloses an injectable composition comprising ethanedial, also called glyoxal, and an aprotic polar solvent such as DMSO (dimethylsulphoxide) in aqueous solution.

Finally, the patent RU 2 116 725 describes a solution based on diethylacetal (or 1,1-diethoxyethane) for embalming bodies.

However, the need still exists for novel products which make it possible to avoid rigidity, pallor, emanations of odours and/or dehydration of the body while having low toxicity for the embalmer and a low cost.

The Applicant has now discovered that it is possible to use at least one compound of the PolyOxymethylene dialkyl ether (POM) type and/or dialdehyde acetals for preserving and/or embalming a human or animal body and thus to remedy one or more of the abovementioned drawbacks.

The POM compounds are known but for different uses. For example, the French patent FR 2 881 750 describes a use of POMs as fuels for fuel cells.

Similarly, dialdehyde acetal compounds are known but, for example, for being used as useful building blocks for organic synthesis (WO 02/42524), as additives (EP0855436), or as adhesives (FR2844802) such as in particular 1,1,2,2-tetra-ethoxyethane.

The invention relates more particularly to the use of at least one compound of formula (I) R—(OCH$_2$)$_n$—OR' wherein R and R', identical or different, represent a linear or branched alkyl radical comprising 1 to 5 carbon atoms and n is an index with a value comprised between 1 and 8, and/or at least one dialdehyde acetal of formula (II):

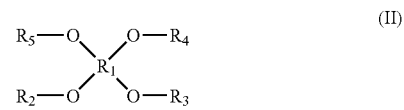

where $R_2$, $R_3$, $R_4$ and $R_5$ designate independently a linear or branched alkyl radical comprising 1 to 8 carbon atoms, or $R_2$ and $R_5$ and/or $R_3$ and $R_4$ form together and with the two oxygen atoms to which they are attached a saturated or unsaturated heterocycle with 5 or 6 members optionally substituted by one or more groups chosen from OH, CH$_2$OH or a linear or branched alkyl radical comprising 1 to 8 carbon atoms; and $R_1$ represents a CH—$R_6$—CH group where $R_6$ forms a bond or represents a linear or branched alkylene radical, comprising 1 to 5 carbon atoms or a saturated or unsaturated carbocycle comprising 3 to 8 carbon atoms; or $R_1$ is a saturated or unsaturated carbocycle comprising 3 to 8 carbon atoms.

Within the context of this description, the term "comprised between" must be interpreted as including the indicated limits.

Within the meaning of the invention, by "preserving" is meant the fact that the enzymatic action is stopped or slowed down in human or tissue animal, compared with untreated tissue, which prevents or slows down the auto-catalytic destruction of this tissue, and/or that the tissues resist outside attacks from bacteria and mycetes better than untreated tissues.

The compounds (I) used according to the invention are PolyOxyMethylene dialkyl ethers which are designated by the initials POM for PolyOxyMethylene to which one or two letters are added (POMXX) making it possible to identify the alkyl radicals(s) R and R', M for methyl, E for ethyl, P or i-P for (iso)propyl, B for butyl, Pe for pentyl and H for hexyl, as well as by an index corresponding to the number n of (CH$_2$O) units (POMXX$_n$).

These products are for example designated:

POMM$_n$ (polyoxymethylene dimethyl ether) when the alkyl is the methyl group, CH$_3$—(OCH$_2$)$_n$—OCH$_3$, POME$_n$ (polyoxymethylene diethyl ether) when the alkyl is the ethyl group, POMP$_n$ (polyoxymethylene dipropyl ether) when the alkyl is the propyl group, POMB$_n$ (polyoxymethylenedibutylether) when the alkyl is the butyl group.

POMM$_n$ is the name given to the compound with n oxymethylene units (formaldehyde). Thus methylal (n=1), is called POMM$_1$, and butylal is called POMB$_1$. If a mixture of products originating from the same synthesis is used, it is called for example POMM$_{3-8/}$ for a mixture containing POMMs with n=3 to 8.

These POMs are dissymmetrical in the case where R is different from R$^1$. It is for example possible to have a $POMME_2$ which designates a polyoxymethylene methyl ethyl ether with two ($CH_2O$) units, i.e. $CH_3$—$(OCH_2)_2$—$OC_2H_5$.

The advantages of POMs are probably linked to their chemical nature which itself depends on their synthesis method, by which it is possible to control the chain length. Generally, the boiling point of POMs increases with the number of formaldehyde ($CH_2O$) units and with the alkyl chain length. On the other hand, the solubility in water diminishes with the (—$CH_2O$—)$_n$ chain length and with the alkyl chain length.

From the point of view of toxicity, methylal ($POMMi$), ethylal ($POME_1$) and butylal ($POMB_1$) are much less toxic than methanol and formaldehyde.

Another advantage of POMs is their low cost. In fact, the synthesis of POMs uses methanol and formaldehyde, itself produced from methanol.

The synthesis of POMs has been well known for a number of years.

In particular, J. F. Walker's book, "FORMALDEHYDE", Robert E. Krieger Publishing Company, Huntington, N.Y., $3^{rd}$ Edition of 1975 is a reference work on the subject. It is in fact possible to find in this reference work a description of the synthesis processes on pages 167 et seq. on the one hand, and 264 et seq. on the other hand. These synthesis processes are based on an acid catalysis of the reaction of an alcohol (methanol or ethanol) or an acetal (methylal or ethylal), with formaldehyde or an equivalent compound. This type of synthesis is also illustrated in numerous patent documents such as U.S. Pat. No. 2,449,469 or JP 47-40772.

Other synthesis methods based on a Lewis acid type catalysis have also been described. There can be mentioned the patent document GB 1120524 which describes the synthesis of stable polyoxymethylene diethers with Lewis acid type ionic catalysts.

Mixed POMs, i.e. those corresponding to the general formula R—$(OCH_2)_n$—OR' with R different from R' are obtained either by direct synthesis according to the processes referred to above, or by transacetalization of two different symmetrical POMs (R=R').

According to an advantageous embodiment, the invention relates to the use of at least one compound chosen from $CH_3$—$(OCH_2)$—$OCH_3$, $CH_3$—$(OCH_2)_2$—$OCH_3$, $CH_3$—$(OCH_2)_3$—$OCH_3$, $CH_3$—$(OCH_2)_4$—$OCH_3$, $CH_3$—$(OCH_2)_5$—$OCH_3$, $CH_3$—$(OCH_2)_6$—$OCH_3$, $CH_3$—$(OCH_2)_7$—$OCH_3$, $CH_3$—$(OCH_2)_8$—$OCH_3$, $C_2H_5$—$(OCH_2)$—$OC_2H_5$, $C_2H_5$—$(OCH_2)_2$—$OC_2H_5$, $C_2H_5$—$(OCH_2)_3$—$OC_2H_5$, $C_2H_5$—$(OCH_2)_4$—$OC_2H_5$, $C_2H_5$—$(OCH_2)_5$—$OC_2H_5$, $C_2H_5$—$(OCH_2)_6$—$OC_2H_5$, $C_2H_5$—$(OCH_2)_7$—$OC_2H_5$, $C_2H_5$—$(OCH_2)_8$—$OC_2H_5$, $C_4H_9$—$(OCH_2)$—$OC_4H_9$, $CH_3$—$(OCH_2)$—$OC_2H_5$, 1,1,2,2-tetraethoxyethane, 1,1,3,3-tetraethoxypropane, 1,1,3,3-tetramethoxypropane, 1,4,9,12-tetraoxadispiro[4,2,4,2]tetradecane, and mixtures thereof and very preferentially from $CH_3$—$(OCH_2)$—$OCH_3$, $CH_3$—$(OCH_2)_2$—$OCH_3$, $C_2H_5$—$(OCH_2)$—$OC_2H_5$, $C_4H_9$—$(OCH_2)$—$OC_4H_9$, 1,1,2,2-tetraethoxyethane, 1,1,3,3-tetraethoxypropane, 1,1,3,3-tetramethoxypropane, 1,4,9,12-tetraoxadispiro[4,2,4,2]tetradecane, and mixtures thereof.

According to an advantageous embodiment, the invention relates to the use of at least one compound of formula R—$(OCH_2)_n$—OR' the structure of which is symmetrical (R=R').

According to a preferred embodiment, the invention relates to the use of a mixture of compounds of formula R—$(OCH_2)_n$—OR in which either R represents a methyl and n ranges from 2 to 8, or R represents an ethyl and n ranges from 1 to 8.

According to a still more preferred embodiment, the invention relates to the use of at least one compound $POMM_{2-8}$ which is a mixture of compounds of formula $CH_3$—$(OCH_2)_n$—$OCH_3$ with n comprised between 2 and 8, the composition of which is as follows:

| n | 2 | 3 | 4 | 5 | 6 | 7 | 8 |
|---|---|---|---|---|---|---|---|
| % | 25-50 | 20-40 | 10-25 | 5-10 | 2-5 | <2 | <1 |

More particularly, a preferred composition of a $POMM_{2-8}$ compound is as follows:

| N | 2 | 3 | 4 | 5 | 6 | 7 | 8 |
|---|---|---|---|---|---|---|---|
| % | 44 | 32 | 14 | 6 | 2.5 | 1 | <1 |

According to a yet more preferred embodiment, the invention relates to the use of at least one $POME_{1-8}$ compound which is a mixture of compounds of formula $C_2H_5$—$(OCH_2)_n$—$OC_2H_5$ with n comprised between 1 and 8, the composition of which is as follows:

| n | 1 | 2 | 3 | 4 | 5 | 6 | 7 | 8 |
|---|---|---|---|---|---|---|---|---|
| % | 58 | 26 | 10 | 4 | 1.5 | <1 | <1 | <1 |

As compounds of formula (II), there can be mentioned, for example, the diacetals of glyoxal (ethanedial), of propanedial, and of glutaraldehyde (pentanedial), in particular those named hereafter of formula:

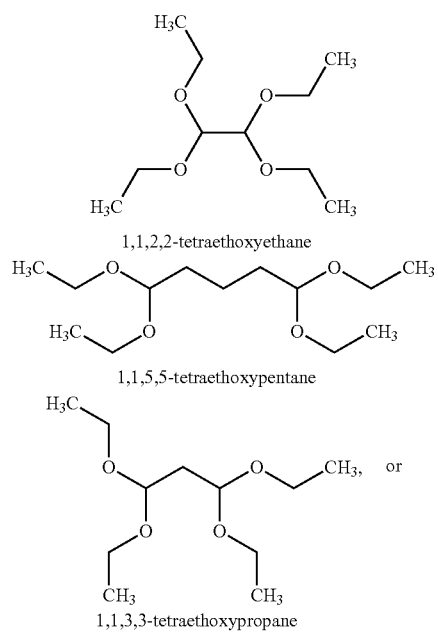

1,1,2,2-tetraethoxyethane 1,1,5,5-tetraethoxypentane 1,1,3,3-tetraethoxypropane

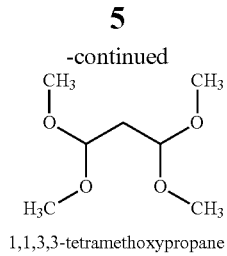

1,1,3,3-tetramethoxypropane the diacetals of malonaldehyde, the diacetals of succinaldehyde, and also the cyclic diacetals of dialdehyde,

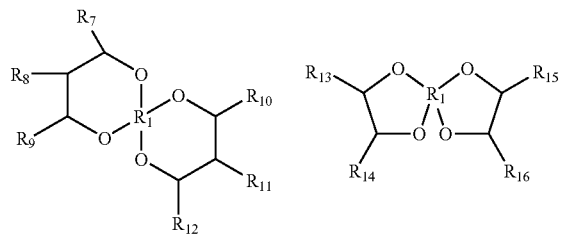

where $R_7$-$R_{16}$ represent independently H, OH, CH$_2$OH or a linear or branched alkyl radical comprising 1 to 8 carbon atoms; and $R_1$ represents a CH—$R_6$—CH group where $R_6$ is defined as previously, such as for example:

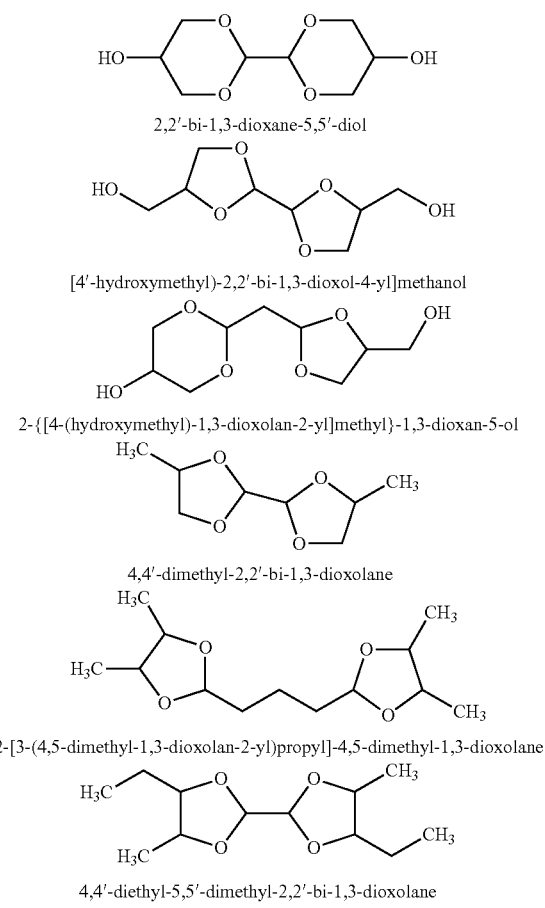

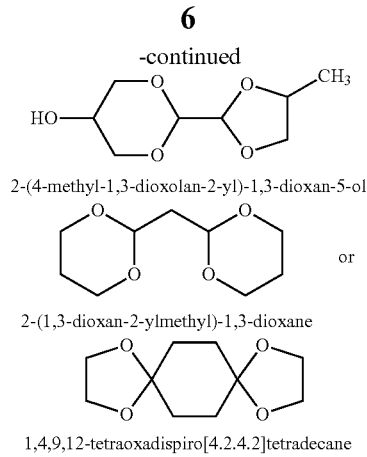

The synthesis methods for the compounds (II) according to the invention are well known. For example, the French Patent Application FR2844802 indicates that diacetals can be obtained by reaction of dialdehydes such as glyoxal, malonaldehyde, or glutaraldehyde with alcohols such as for example monoalcohols such as methanol, ethanol, diols such as ethyleneglycol, diethyleneglycol, 1,4-butanediol, neopentylglycol, or polyols such as glycerol, penta-erythritol.

The present invention also relates to a composition comprising at least one of said compounds of formula (I) and/or (II) and glycerol.

According to an advantageous embodiment, the composition comprises 12-70% by volume of at least one compound of formula (I) and/or (II), 10-15% by volume of glycerol, 15-75% by volume of at least one alcohol such as for example ethanol, propanol and isopropanol and 0-10% by volume of at least one colouring agent such as for example sunset yellow FCF, titanium dioxide and zinc oxide and/or an aroma producer such as in particular mint, coriander, thyme, lemon grass and grapefruit.

This composition can moreover contain various constituents such as an antiseptic agent, which is advantageously a soap; a humectant such as ethylene glycol and a polyethylene glycol; and mixtures thereof.

Another subject of the invention relates to a process for preserving a human or animal body and/or embalming a dead body comprising the administration to the body of a composition comprising at least one compound of formula (I) and/or formula (II) in which $R_1$, $R_2$, $R_3$, $R_4$ and $R_5$ are as described previously.

Two advantages of the process according to the invention are the rapidity of execution, i.e. that the speed of decoagulation is significant, as well as the rapidity of care.

In a first advantageous embodiment, the composition is injected by intra-arterial route into the body.

Preferentially, the composition injected by arterial route is an aqueous solution the concentration of which in compounds of formula (I) and/or in compounds of formula (II) ranges from 1 to 25% by weight. Still more preferentially, the composition is injected pure into a cavity.

In a second advantageous embodiment, the composition is perfused into the body.

In a third advantageous embodiment, the body is immersed in the composition.

In a fourth advantageous embodiment, the composition is applied to the body by topical route.

These methods of administration are well known to a person skilled in the art.

The examples which follow are given purely by way of illustration and are in no way limitative of the invention.

EXAMPLES

Example 1

A composition comprising 600 ml of POMM, 200 ml of glycerol, 100 ml of saline solution, 80 ml of soap and 20 ml of colorant and vegetable oil is injected by intra-arterial route into the dead body of a pig.

Example 2

The dead body of a duck is painted with a composition comprising 600 ml of 1,1,2,2-tetraethoxyethane available from Acros Organics, 200 ml of glycerol, 100 ml of saline solution, 80 ml of soap and 20 ml of colorant and of vegetable oil.

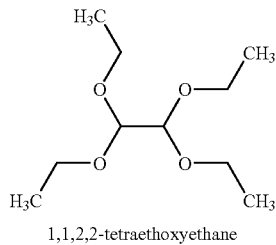

1,1,2,2-tetraethoxyethane

Example 3

Example 2 is reproduced, replacing 1,1,2,2-tetraethoxyethane with 1,1,3,3-tetraethoxypropane (available from Acros Organics).

1,1,3,3-tetraethoxypropane (CAS RN 122-31-6), available from Acros Organics, has a boiling point of 220° C. and a flash point of 88° C.

Example 4

Example 2 is reproduced, replacing 1,1,2,2-tetraethoxyethane with 1,1,3,3-tetramethoxypropane (available from Acros Organics).

1,1,3,3-tetramethoxypropane (CAS RN 102-52-3), available from Acros Organics, has a boiling point of 183° C. and a flash point of 60° C.

Example 5

The dead body of a duck is painted with a composition comprising 600 ml of 1,4,9,12-tetraoxadispiro[4,2,4,2]tetradecane (available from Maybridge SCR), 200 ml of glycerol, 100 ml of saline solution, 80 ml of soap, and 20 ml of colorant and vegetable oil.

Example 6

A dilution of a preservation fluid which consists either of $POMM_{2-8}$, or of $POME_{1-8}$ is prepared, by mixing 800 ml of fluid with 800 ml of tepid water.

The composition of the $POMM_{2-8}$ used is as follows:

| n | 2 | 3 | 4 | 5 | 6 | 7 | 8 |
|---|---|---|---|---|---|---|---|
| % | 44 | 32 | 14 | 6 | 2.5 | 1 | <1 |

The composition of the $POMM_{1-8}$ used is as follows:

| n | 1 | 2 | 3 | 4 | 5 | 6 | 7 | 8 |
|---|---|---|---|---|---|---|---|---|
| % | 58 | 26 | 10 | 4 | 1.5 | <1 | <1 | <1 |

The preservation fluid is injected into the dead bodies of men and women of various ages, by electric injection. This injection is carried out using an electric pump.

The injection is followed by drainage to the outside.

The operation lasts only 30 minutes, which is relatively rapid.

Observations are made on the following days (D+1 to D+5 depending on the case).

All of the treatment and observation conditions are summarized in the following table:

| Age | 60 years | 60 years | 70 years | 67 years | 54 years | 70 years | 75 years |
|---|---|---|---|---|---|---|---|
| Sex | F | M | F | F | M | M | F |
| Physical examination | Haematoma | Jaundice | Haematoma | Discolouration* | Discolouration** | Healthy body | Healthy body |
| Height (cm) | 170 | 175 | 170 | 165 | 180 | 180 | 160 |
| Weight (kg) | 100 | 60 | 80 | 60 | 85 | 80 | 60 |
| Product | POME1-8 | POMM2-8 | POMM2-8 | POMM2-8 | POMM2-8 | POMM2-8 | POMM2-8 |
| Injection technique | Femoral carotid | Femoral | Femoral | Carotid | Carotid | Carotid | Femoral |
| Electric injection | yes | yes | yes | yes | yes | yes | yes |
| Drainage method | Cardiac | Cardiac | Cardiac | Venous cardiac (jugular) | Venous cardiac (jugular) | Cardiac | Cardiac |
| Quantity injected (L) | 8 | 7.5 | 7.5 | 8 | 8 | 5 | 5 |
| Concentration (% weight in water) | 3.8 | 3.8 | 3.8 | 5 | 5 | 5 | 5 |
| Volume in cavity (l) | 0.5 | 0.5 | 0.5 | 0.4 | 0.3 | 0.3 | 0.3 |
| Concentration (% weight) | 100 | 100 | 100 | 100 | 100 | 100 | 100 |

| Quantity drained (1) | 1.6 | 2 | 6 | 5 | 6.5 | 3 | 3 |
|---|---|---|---|---|---|---|---|
| Observations D = 0 date of the injection | Nothing to report at D + 2 | Nothing to report at D + 2, no odour, no change in coloration of the body | D + 1, D + 2, D + 4, D + 5 Same findings: no odour, no traces of dehydration or putrefaction, no gas, appearance very good | D + 1, D + 3, D + 4, D + 5 Same findings, no preservation problems | D + 1, D + 2, D + 3 Same findings: no preservation problems | D + 2 No preservation problems | D + 3 No preservation problems |

*death by gastric haemorrhage
**very pronounced cyanoses, acute nicotinism, under anticoagulant treatment According to this table, it is noted that even several days after the injection of the preservation fluid, no change in the appearance of the body, no cadaverous odour, no trace of mould, and no discharge from the orifices of the face or the lower abdomen is observed.

In particular, the surface tissues are also extremely supple and the lips have remained fine. Moreover, the skin remains slightly tinted by the fluid, without it being necessary to resort to makeup cream.

The compounds according to the invention thus make it possible to make the body-embalming operation easy and rapid.

The invention claimed is:

1. A process for preserving a dead human or animal body and/or embalming a dead human or animal body comprising the administration to said dead body of a composition comprising at least one compound of formula
    (I) R—$(OCH_2)_n$—OR' wherein R and R', identical or different, represent a linear or branched alkyl radical comprising 1 to 5 carbon atoms and n is an index with a value comprised between 1 and 8.

2. The process according to claim 1, characterized in that the composition is injected into said body by intra-arterial route.

3. The process according to claim 1, characterized in that the composition is perfused into said body.

4. The process according to claim 1, characterized in that said body is immersed in the composition.

5. The process according to claim 1, characterized in that the composition is applied to said body by topical route.

6. The process according to claim 1, wherein the at least one compound is selected from the group consisting of $CH_3$—$(OCH_2)$—$OCH_3$, $CH_3$—$(OCH_2)_2$—$OCH_3$, $CH_3$—$(OCH_2)_3$—$OCH_3$, $CH_3$—$(OCH_2)_4$—$OCH_3$, $CH_3$—$(OCH_2)_5$—$OCH_3$, $CH_3$—$(OCH_2)_6$—$OCH_3$, $CH_3$—$(OCH_2)_7OCH_3$, $CH_3$—$(OCH_2)_8$—$OCH_3$, $C_2H_5$—$(OCH_2)$—$OC_2H_5$, $C_2H_5$—$(OCH_2)_2$—$OC_2H_5$, $C_2H_5$—$(OCH_2)_3$—$OC_2H_5$, $C_2H_5$—$(OCH_2)_4$—$OC_2H_5$, $C_2H_5$—$(OCH_2)_5$—$OC_2H_5$, $C_2H_5$—$(OCH_2)_6$—$OC_2H_5$, $C_2H_5$—$(OCH_2)_7$—$OC_2H_5$, $C_2H_5$—$(OCH_2)_8$—$OC_2H_5$, $C_4H_9$—$(OCH_2)$—$OC_4H_9$, $CH_3$—$(OCH_2)$—$OC_2H_5$.

7. The process according to claim 1, wherein the at least one compound is of formula (I) and has a symmetrical structure.

8. The process according to claim 1, wherein the at least one compound is a mixture of compounds of formula $CH_3$—$(OCH_2)_n$—$OCH_3$ where n is 2-8.

9. The process according to claim 1, wherein the at least one compound is a mixture of compounds of formula $C_2H_5$—$(OCH_2)_n$—$OC_2H_5$ where n is 1-8.

* * * * *